(12) United States Patent
Martin Benlloch et al.

(10) Patent No.: US 6,676,661 B1
(45) Date of Patent: Jan. 13, 2004

(54) MULTIAXIAL CONNECTOR FOR SPINAL IMPLANT

(76) Inventors: Antonio Martin Benlloch, Musico Gines 9, Pte 43, Valence (ES), E-46022; Jean-Yves Leroy, 49 rue du Bourrelier, Campagne les Hesdin (FR), F-62870; Inmaculada Perez Pedron, Urb. Alton Blancos, 1° Ed. PTA 10 DCHA C/Trragona No. 11, el Campo-Alicante (ES), E-03580; Guy Viart, 6 rue de Vaulx Vraucourt, St. Leger (FR), F-62128

( * ) Notice: Subject to any disclaimer, the term of this patent is extended or adjusted under 35 U.S.C. 154(b) by 185 days.

(21) Appl. No.: 10/031,395

(22) PCT Filed: Jun. 26, 2000

(86) PCT No.: PCT/FR00/01781

§ 371 (c)(1),
(2), (4) Date: Jan. 30, 2002

(87) PCT Pub. No.: WO01/06939

PCT Pub. Date: Feb. 1, 2001

(30) Foreign Application Priority Data

Jul. 23, 1999 (FR) .............................................. 99 09755

(51) Int. Cl.⁷ .......................... A61B 17/70; A61B 17/86
(52) U.S. Cl. .......................................... 606/61; 606/73
(58) Field of Search .............................. 606/61, 60, 59, 606/72, 73, 70, 71

(56) References Cited

U.S. PATENT DOCUMENTS

| | | | | |
|---|---|---|---|---|
| 5,474,551 A | * | 12/1995 | Finn et al. ...................... | 606/61 |
| 5,501,684 A | * | 3/1996 | Schlapfer et al. .............. | 606/73 |
| 5,540,688 A | * | 7/1996 | Navas .......................... | 606/61 |
| 5,741,255 A | * | 4/1998 | Krag et al. .................... | 606/61 |
| 5,776,135 A | * | 7/1998 | Errico et al. ................... | 606/61 |
| 5,800,435 A | * | 9/1998 | Errico et al. ................... | 606/61 |
| 5,938,663 A | * | 8/1999 | Petreto ......................... | 606/61 |
| 6,063,089 A | * | 5/2000 | Errico et al. ................... | 606/61 |
| 6,267,765 B1 | * | 7/2001 | Taylor et al. .................. | 606/61 |
| 6,379,357 B1 | * | 4/2002 | Bernstein et al. .............. | 606/61 |

FOREIGN PATENT DOCUMENTS

| | | |
|---|---|---|
| EP | 0468264 | 1/1992 |
| FR | 2761590 | 10/1998 |
| FR | 2765093 | 12/1998 |

* cited by examiner

Primary Examiner—Pedro Philogene
Assistant Examiner—D. Austin Bonderer
(74) Attorney, Agent, or Firm—Ralph A. Dowell; Dowell & Dowell PC

(57) ABSTRACT

A multiple axis connector for securing a connecting rod of a spinal implant to a vertebra anchor wherein the connector includes a first element for securing to the vertebra anchor and a second element for receiving the connecting rod and which elements are joined by a ball joint member which permits relative angular adjustment therebetween.

6 Claims, 3 Drawing Sheets

MULTIAXIAL CONNECTOR FOR SPINAL IMPLANT

The present invention relates to a multiaxis connector for forming a spinal implant equipped with connecting rods.

French patent no. 2 731 344 discloses a spinal implant allowing angular orientation of a connecting rod with respect to the bone anchoring elements.

The anchoring element consists of a fixing screw comprising an anchorage part separated from a protruding threaded head, associated with a clamping nut via an intermediate body of polygonal cross section forming a stop.

The anchoring element also comprises a receiving ring which collaborates with the protruding threaded head of the anchorage part and allows the connecting rod to be fitted.

The receiving ring has two branches connected by a connecting zone to form an element that forms a clip. The two branches are pierced with coaxial facing holes designed to have the protruding threaded head of the fixing screw pass through them and to bear against the polygonal stop.

The connecting zone of the two branches of the ring delimits, at right angles to the facing holes, a bore collaborating with a compressible sleeve equipped with a central passage designed to accommodate the connecting rod.

Assembling the sleeve inside the bore of the ring is intended to create a ball-joint connection so that before the nut is tightened onto the protruding threaded head of the fixing screw, the connecting rod can be positioned in a determined angular position.

The spinal implant described hereinabove has certain disadvantages as regards the fitting of the sleeve inside the bore of the ring forming the ball-joint connection for the pivoting of the connecting rod. Specifically, it is found that this assembly does not allow the connecting rod sufficient travel when the spinal implant is being fitted, because said rod butts against the upper and lower outer edges of the bore.

It is these disadvantages that the present invention intends more specifically to remedy.

Specifically, the multiaxis connector for a spinal implant according to the present invention is intended, on the one hand, to be able to pivot in all directions with respect to the vertebral bodies and, on the other hand, to allow large-amplitude pivoting of the connecting rod with respect to said connector.

The multiaxis connector according to the present invention comprises:
- a connecting rod, a fixing screw comprising a first threaded part for anchoring it in the bone tissue, an intermediate head with a hexagonal profile and a second threaded part receiving a clamping nut;
- a first connecting element pierced with a bore designed to receive the second threaded part of the fixing screw, with another bore, comprising, in its interior part, an annular track of spherical profile, and with a slot passing through the bore to open into the bore at the annular track;
- a second connecting element pierced with a bore designed to receive the connecting rod, with a threaded hole collaborating with a binding screw for immobilizing said rod in terms of translation;
- and connecting means forming a ball joint which, on the one hand, allow the first and second connecting elements to be coupled to one another in such a way that said elements can pivot one with respect to the other so as to present the connecting rod in determined angular positions and, on the other hand, allow the connecting rod to be offset laterally with respect to the center of pivoting of said elements.

The multiaxis connector according to the present invention comprises a second connecting element provided with connecting means which consist, on one of the exterior faces of said element, of a finger extended by a head with a spherical profile so that said head can collaborate with the spherical track of the bore of the first connecting element.

The multiaxis connector according to the present invention comprises a first element, the bore of which has cylindrical bearing surfaces on which the clamping nut and the intermediate stop of the fixing screw respectively bear when the connecting means are immobilized in terms of rotation by the tightening of said nut.

The multiaxis connector according to the present invention comprises a first connecting element which, on each side of the slot, has branches joined together by a curved wall, said branches being able to deform under the clamping force of the nut of the fixing screw to immobilize the connecting means in terms of rotation.

The multiaxis connector according to the present invention comprises a first connecting element, the slot of which is arranged in a plane which intersects the main axes of the bores at right angles.

The multiaxis connector according to the present invention comprises a second connecting element, the threaded hole of which opens into the bore in a perpendicular direction.

The description which will follow with reference to the appended drawings, given by way of nonlimiting example, will allow better understanding of the invention, of the characteristics that it has and of the advantages it is likely to afford.

BRIEF DESCRIPTION OF THE DRAWINGS

FIGS. 1 to 3 show a multiaxis connector 1 which, together with other connectors of the same kind, allows a connecting rod 2 to be secured for producing a spinal implant A. Each multiaxis connector 1 of the spinal implant A is fixed to the body of a vertebra B of a spinal column.

Figure 1:
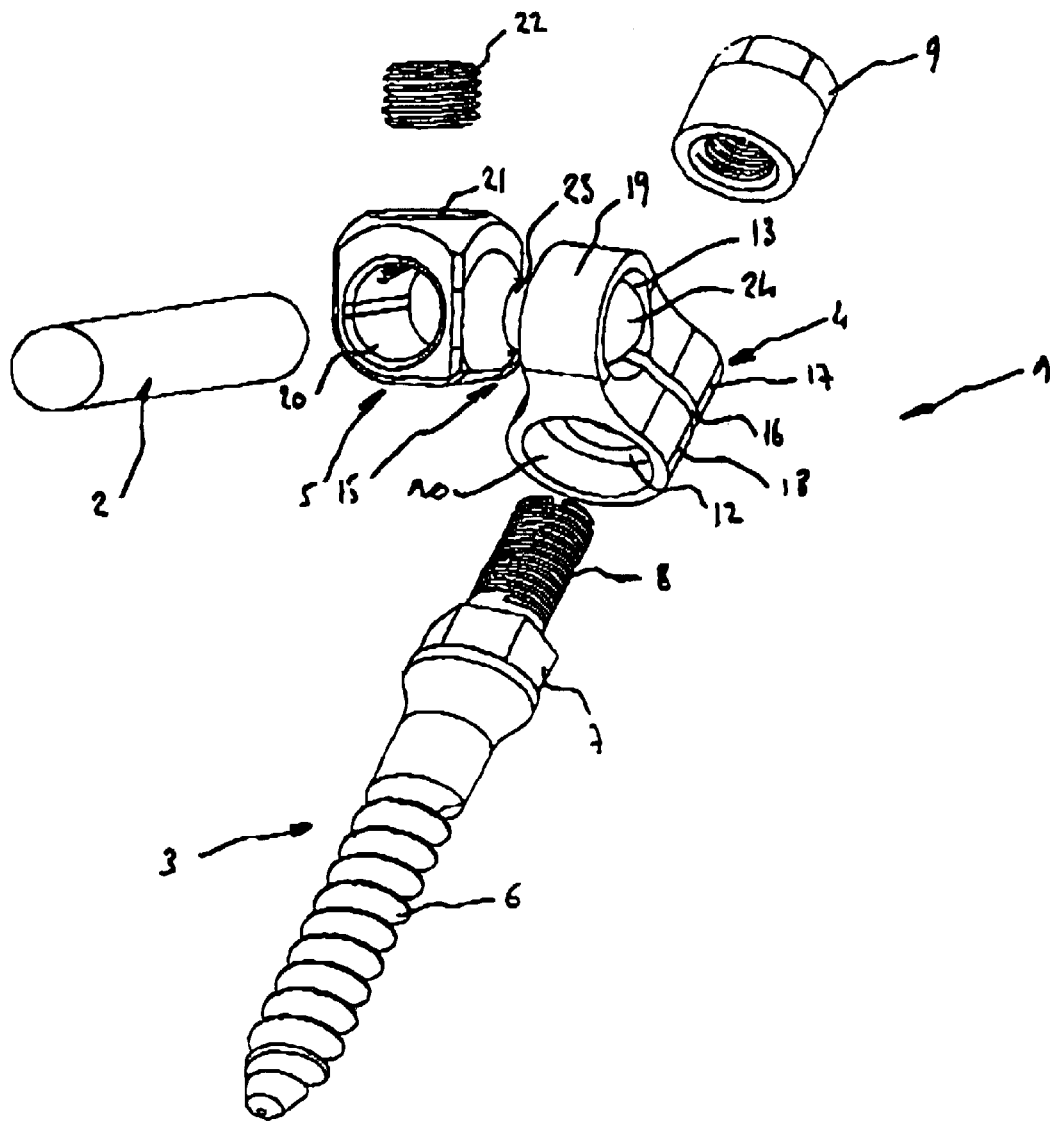
FIG. 1 is an exploded perspective view illustrating the multiaxis connector for a spinal implant according to the present invention.
Figure 2:
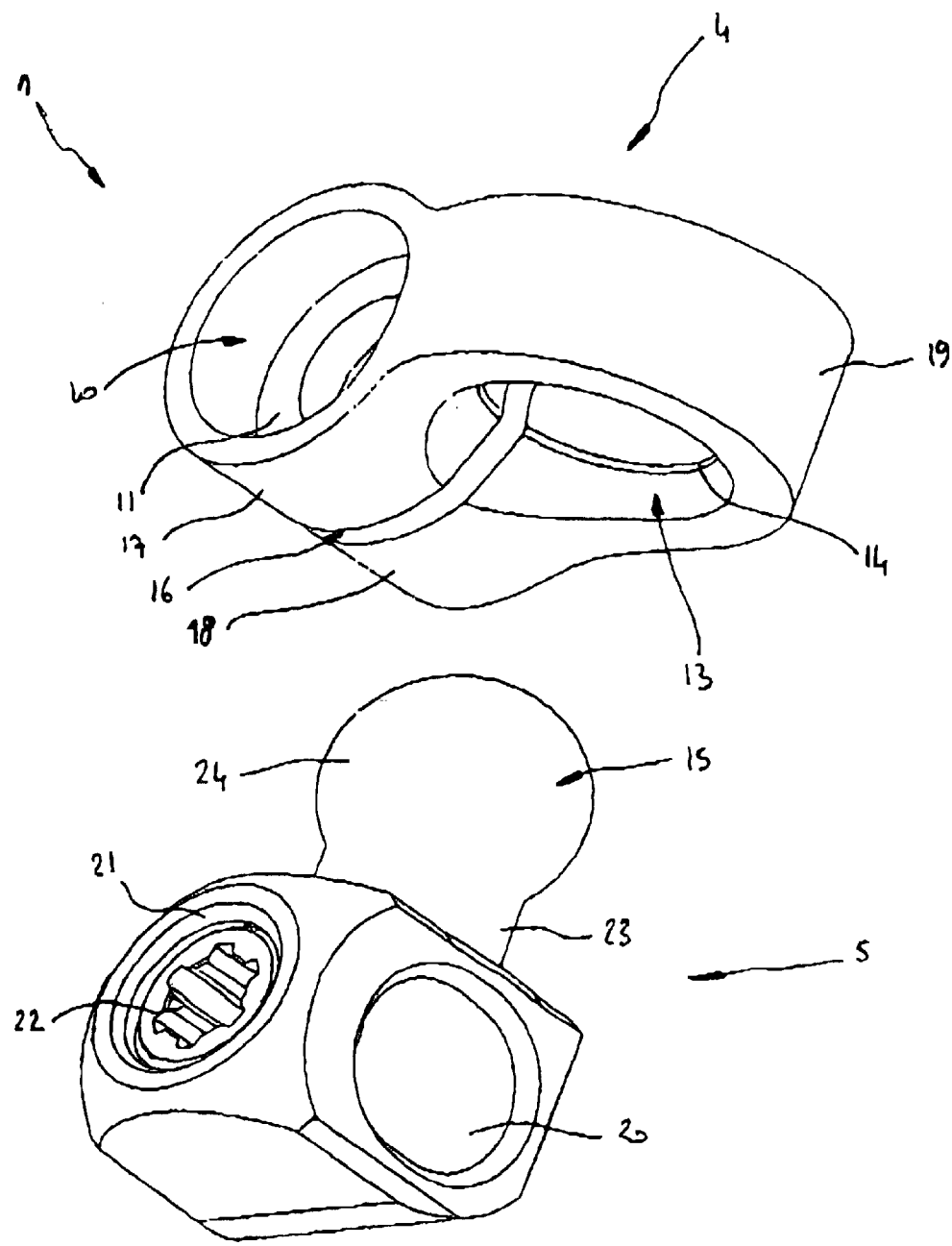
FIG. 2 is an exploded perspective view showing, in detail, the first and second connecting elements of the multiaxis connector for a spinal implant according to the present invention.
Figure 3:
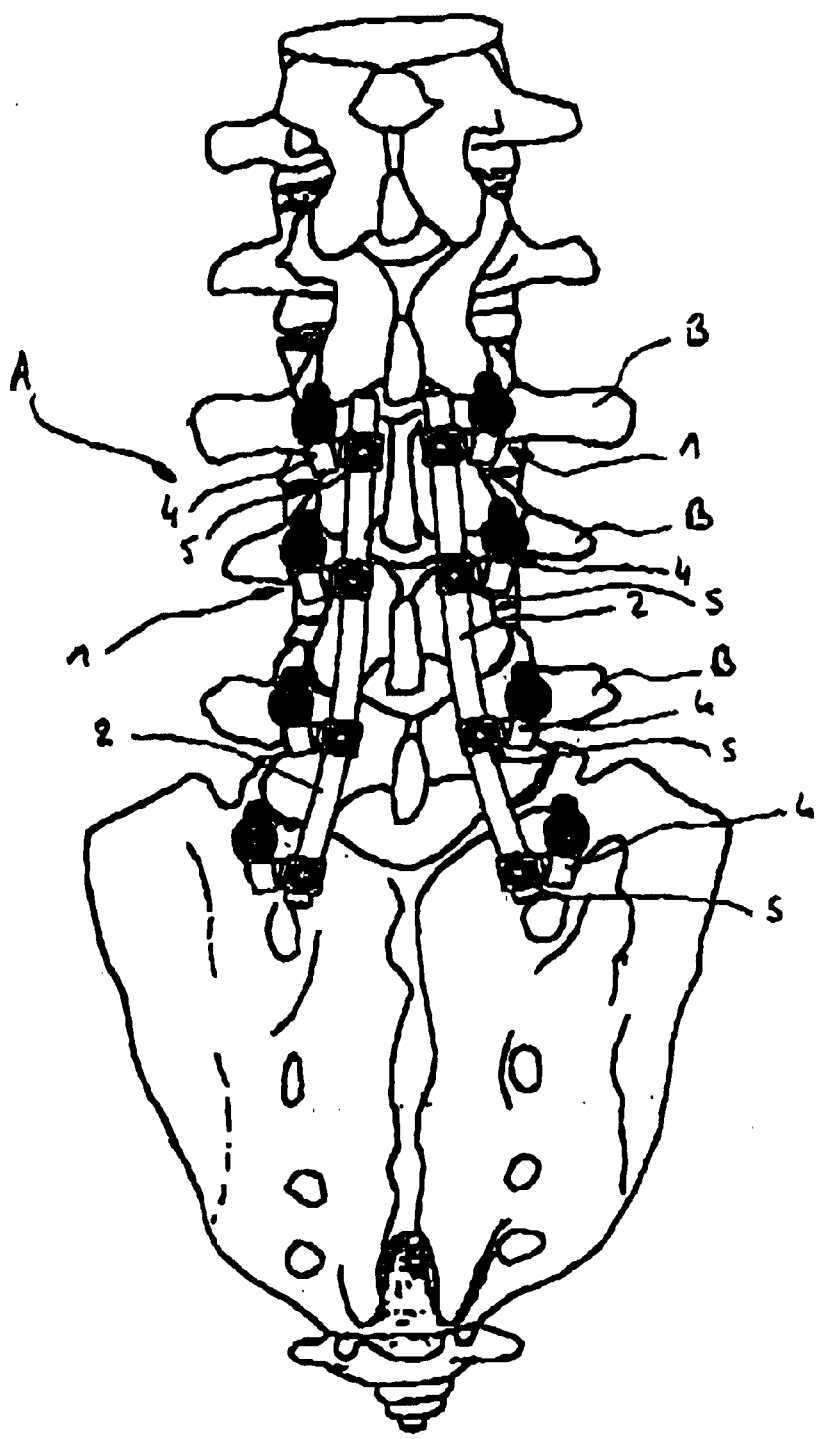
FIG. 3 is a view depicting the multiaxis connectors of a spinal implant which are fixed to the vertebrae of a spinal column.

Thus, each multiaxis connector 1 of the spinal implant A comprises a fixing screw 3, first and second connecting elements 4, 5 for accommodating the connecting rod 2 and connecting means 15 forming a ball joint for the coupling-together and pivoting of the elements 4, 5.

The fixing screw 3 comprises a first threaded part 6 for anchoring it into the bone tissue of a vertebra B, an intermediate head 7 with a hexagonal profile forming a stop, and a second threaded part 8 extending in the continuation of and above said stop.

The intermediate head 7 allows the fixing screw 3 to be turned so that the threaded part 6 enters the bone tissue of the corresponding vertebra B.

The second threaded part 8 is designed to take a nut 9 for fixing the first connecting element 4 to the screw 3, which connecting element bears against the intermediate head 7.

The first connecting element 4 is pierced with an open bore 10, comprising cylindrical bearing surfaces 11, 12 on which the clamping nut 9 and the intermediate head 7 of the fixing screw 3 respectively bear when this fixing screw passes through the bore 10.

The connecting element 4 is pierced at right angles to the bore 10 with another open bore 13 which, in its interior part and at its center, comprises an annular track 14, the profile of which is the shape of a portion of a sphere.

The connecting element 4 comprises a slot 16 passing through the bore 10 and opening into the bore 13 at the annular track 14. Thus, the connecting element 4 has, on each side of the slot 16, branches 17, 18 joined together by a curved wall 19 delimiting the bore 19. The branches 17, 18 obviously each have the bore 10 for the passage of the fixing screws 3 passing through them.

The slot 16 is arranged in a plane which intersects the main axes of the open bores 10 and 13 at right angles.

The slot 16 allows the connecting element 4 to be given a certain flexibility so that it can deform under the clamping force of the nut 9 of the fixing screw 3 so that said connecting element 4 constitutes a clip allowing the connecting means 15 secured to the connecting element 5 to be immobilized angularly as will be seen better later on.

The connecting element 5 of the multiaxis connector 1 is pierced with an open bore 20 intended to accommodate the connecting rod 2 of the spinal implant A.

The connecting element 5 is pierced at right angles to the bore 20 with a threaded hole 21 which opens into said bore and which is designed to accommodate a binding screw 22 for immobilizing the connecting rod 2 in terms of translation with respect to the connecting element.

The connecting element 5 comprises connecting means 15 which consist, on one of the exterior faces of said element, of a finger 23 extended by a head 24 with a spherical profile.

The first connecting element 4 is held against a vertebra B of a patient using the fixing screw 3 which passes through the bore 10 provided for that purpose.

The first connecting element 4, before the nut 9 has been tightened onto the second threaded part 8 of the fixing screw 3, takes the second connecting element 5 via the connecting means 15 consisting of the spherical head 24 which collaborates with the track 14 with the spherical profile formed on the inside of the bore 13 of said first connecting element.

The fixing means 15 make it possible, on the one hand, to couple the two connecting elements 4, 5 of the multiaxis connector 1 together and, on the other hand, to produce between the two connecting elements a ball-joint connection for angular adjustment of the connecting rod 2.

The connecting means 15 also make it possible for the connecting rod 2 to be moved laterally with respect to the center of pivoting of the connecting elements 4, 5 so that said rod can have a large angular travel.

The connecting rod 2 is introduced into the bore 20 of the connecting element 5 and held transversely therein via the binding screw 22 which is screwed into the threaded hole 21.

When the angular position of the connecting rod 2 is determined by the rotating of the spherical head 24 inside the spherical track 14 of the bore 13, the nut 9 is tightened onto the threaded head 8 of the fixing screw 3 in such a way as to deform the first connecting element 4 by means of the slot 16 so as to immobilize the spherical head 24 inside the track 14.

When the connecting means 15 are immobilized, it is noted that the stop 7 and the nut 9 of the fixing screw 3 come respectively to bear against the bearing surfaces 11 and 12 of the bore 10.

It will be noted during the tightening of the nut 9 of the fixing screw 3 that the connecting elements 4 and 5 do not come into contact with the articulation of the corresponding vertebra a because of the position of the stop 7 on said screw.

What is claimed is:

1. A multiaxial connector for producing a spinal implant (A) to keep a connecting rod (2) in determined angular positions with respect to the vertebral bodies (B), said connector (1) being fixed to each vertebral body (B) by a fixing screw (3) comprising a first threaded part (6) for anchoring it into the bone tissue, an intermediate head (7) of hexagonal profile and a second threaded part (8) that takes a clamping nut (9), characterized in that it comprises:

a first connecting element (4) pierced with a bore (10) designed to receive the second threaded part (8) of the fixing screw (3), with another bore (13), comprising, in its interior part, an annular track (14) of spherical profile, and with a slot (16) passing through the bore (10) to open into the bore (13) at the annular track (14);

a second connecting element (5) pierced with a bore (20) designed to receive the connecting rod (2), with a threaded hole (21) collaborating with a binding screw (22) for immobilizing said rod in terms of translation;

and connecting means (15) forming a ball joint which, on the one hand, allow the first and second connecting elements (4, 5) to be coupled to one another in such a way that said elements can pivot one with respect to the other so as to present the connecting rod (2) in determined angular positions and, on the other hand, allow the connecting rod (2) to be offset laterally with respect to the center of pivoting of said elements (4, 5).

2. The multiaxis connector as claimed in claim 1, characterized in that the second connecting element (5) comprises connecting means (15) which consist, on one of the exterior faces of said element, of a finger (23) extended by a head (24) with a spherical profile so that said head can collaborate with the spherical track (14) of the bore (13) of the first connecting element (4).

3. The multiaxis connector as claimed in claim 1, characterized in that the bore (10) comprises cylindrical bearing surfaces (11, 12) on which the clamping nut (9) and the intermediate stop (7) of the fixing screw (3) respectively bear when the connecting means (15) are immobilized in terms of rotation by the tightening of said nut (9).

4. The multiaxis connector as claimed in claim 1, characterized in that the connecting element (4) has, on each side of the slot (16), branches (17, 18) joined together by a curved wall (19), said branches being able to deform under the clamping force of the nut (9) of the fixing screw (3) to immobilize the connecting means (15) in terms of rotation.

5. The multiaxis connector as claimed in claim 1, characterized in that the slot (16) is arranged in a plane which intersects the main axes of the bores (10, 13) of the connecting element (4) at right angles.

6. The multiaxis connector as claimed in claim 1, characterized in that the threaded hole (21) of the second connecting element (5) opens into the bore (20) in a perpendicular direction.

* * * * *